United States Patent
Goedknegt et al.

(10) Patent No.: US 12,141,346 B2
(45) Date of Patent: Nov. 12, 2024

(54) VISION CORRECTION DISPLAY DEVICE, EYE-TRACKING SYSTEM AND METHOD TO COMPENSATE FOR VISUAL IMPAIRMENTS

(71) Applicant: RABBIT EYES B.V., Rotterdam (NL)

(72) Inventors: Lennard Goedknegt, Rotterdam (NL); Richard Mendes, Paramaribo (SR); Alexander M. J. Spaans, Rotterdam (NL)

(73) Assignee: RABBIT EYES B.V., Rotterdam (NL)

( * ) Notice: Subject to any disclaimer, the term of this patent is extended or adjusted under 35 U.S.C. 154(b) by 0 days.

(21) Appl. No.: 18/032,214

(22) PCT Filed: Oct. 11, 2021

(86) PCT No.: PCT/EP2021/077977
§ 371 (c)(1),
(2) Date: Apr. 17, 2023

(87) PCT Pub. No.: WO2022/084076
PCT Pub. Date: Apr. 28, 2022

(65) Prior Publication Data
US 2023/0409109 A1    Dec. 21, 2023

(30) Foreign Application Priority Data
Oct. 20, 2020   (NL) ...................................... 2026709

(51) Int. Cl.
*G06F 3/01* (2006.01)

(52) U.S. Cl.
CPC .............. *G06F 3/013* (2013.01); *G06F 3/016* (2013.01)

(58) Field of Classification Search
CPC .................................. G06F 3/013; G06F 3/016
See application file for complete search history.

(56) References Cited

U.S. PATENT DOCUMENTS

2015/0262424 A1* 9/2015 Tabaka ............... G02B 27/0075
345/633
2020/0272232 A1* 8/2020 Lussier .............. G02B 27/0025

OTHER PUBLICATIONS

International Preliminary Report on Patentability from corresponding PCT Application No. PCT/EP2021/077977, dated Apr. 13, 2023.
International Search Report from corresponding PCT Application No. PCT/EP2021/077977, dated Jan. 27, 2022.
Written Opinion from corresponding PCT Application No. PCT/EP2021/077977, dated Jan. 27, 2022.

\* cited by examiner

*Primary Examiner* — Lisa S Landis
(74) *Attorney, Agent, or Firm* — Harness, Dickey & Pierce, P.L.C.

(57) ABSTRACT

The invention relates to a display device for displaying an image for a user having a visual impairment. The display device comprises a pixelated display, a processor, an eye-tracking system and a microlens array. The invention is also related to a method for displaying an image for a user having a visual impairment on a display device. The invention is further related to a user having a visual impairment and a computer program for performing the method of the invention.

16 Claims, 6 Drawing Sheets

VISION CORRECTION DISPLAY DEVICE, EYE-TRACKING SYSTEM AND METHOD TO COMPENSATE FOR VISUAL IMPAIRMENTS

The current invention is related to a display device for displaying an image for a user having a visual impairment. The invention is also related to a method for displaying an image for a user having a visual impairment on a display device. The invention is further related to a processor for operating a display device adapted for displaying an image for a user having a visual impairment and a computer program for performing the method of the invention.

The world is digitalizing at a fast pace and life without electronic displays has become unimaginable. Smart devices that incorporate such electronic displays, such as mobile phones and tables, have changed the lives of many people and has enabled a new generation of workers to be productive in the workplace.

Some people experience visual impairments such as hyperopia, presbyopia and cataracts. A substantial portion of the population is at risk from suffering from visual impairments. For example, people from their mid-thirties onwards have an elevated risk of experiencing a visual impairment associated with old age.

These visual impairments make it more difficult to focus on objects such as on electronic displays. This inhibits these people in their day to day lives. The operating systems of some of these electronic displays have features to alleviate some of the problems associated with visual impairments. For example, a size, brightness and contrast may be adjusted in order to make an image easier viewable for a person. Other features include displaying text of an image in bold, changing the color pallet and using speech technology.

WO 2019/171342 discloses a digital display device to render an input image for viewing by a viewer having reduced visual acuity. The display device comprises a digital display medium comprising an array of pixels, a microlens array disposed relative to said digital display and a hardware processor operable to render an image on the digital display medium so to produce a designated image perception adjustment to at least partially address the viewer's reduced visual acuity. A dimension of each microlens is selected to minimize a spot size on a retina of the viewer produced by the digital display medium.

US 2015/0262424 A1 discloses a head-mountable device provided for augmenting a contemporaneously viewed real image of an object in a real-world environment using a light field display system that allows for depth and focus discrimination. The device may include a light-producing display engine, a viewing location element, and a microlens array.

US 2020/0272232 A1 discloses various embodiments of a light field display, adjusted pixel rendering method and computer readable medium therefor, and vision correction system and method using same addressing astigmatism or similar conditions. In one embodiment, a computer implemented method is provided to automatically adjust user perception of an input image to be rendered on a digital display via a set of pixels thereof.

A downside of the digital display device known in the art is that, when the user moves relative to the display device, the user observes the images from a different angle which has a negative impact on the viewing experience and reduces the ability of the user to view the image in focus.

The invention provides a display device for displaying an image for a user having a visual impairment which alleviates the abovementioned downside. The display device according to the invention is described in claim 1.

The display device according to the invention is adapted for displaying an image for a user having a visual impairment. The display device comprises a pixelated display which comprises an array of pixels. Each pixel of the pixelated display comprises a number of subpixels, for example three subpixels, for example red, green and blue subpixels. By allowing the subpixels to emit light with a certain intensity, the corresponding subpixel value, the pixel may appear to emit light of varying color. The pixelated display of the display device is operable to display the image to an eye of the user located at a viewing location relative to a position of the pixelated display.

The display device further comprises a processor for operating the pixels of the pixelated display to display the image on the pixelated display. For example, the processor may be a processor of a smart device, such as a smart phone or a smartwatch. The processor may also be a processor dedicated to the functioning of the display device. The processor is operable to store information on the eye of the user such as focal length of the eye and size of the eye or size of the pupil. For example, the display device, when turned on for the first time, may prompt the user to take a few tests to determine the focal length and the size of the eye of the user. It may also be possible to manually store and change the focal length and the size of the eye of the user. In embodiments the processor may be adapted to store additional information on the user, such as additional information on the visual impairment of the user. In an embodiment the processor may further be adapted to store information on various users. The processor may be adapted to recognize various users, for example by facial recognition, and load the correct stored focal length and eye size.

The display device further comprises an eye-tracking system adapted for determining changes in the viewing location of the eye of the user relative to the position of the pixelated display. The eye-tracking system may for example be integrated in a camera system of a smart phone or a virtual reality headset comprising the display device. The eye-tracking system may also be a dedicated eye-tracking system. The eye-tracking system may continuously monitor changes in the position of the eye of the user, or the eye-tracking system may monitor changes in the position of the eye of the user at regular, or even irregular, intervals for example at 2 second intervals, or at 5 second intervals.

The display device further comprises a microlens array provided on the pixelated display. The microlens array comprises microlenses that are arranged in a two-dimensional plane oriented parallel to the pixelated display. The microlens array covers, preferably completely covers, the pixelated display. The microlens array is configured to project light emitted by the pixelated display towards the eye of the user in the viewing location.

The display device according to the invention comprises an eye-tracking system adapted for determining changes in the viewing location of the eye of the user relative to the position of the pixelated display. The eye-tracking system may track the position of the eyes of the user and thus may track the position of the head of the user relative to the display device. This allows the display device to determine when a viewing position of the user relative to the display device changes.

The processor may determine values of subpixels of the pixelated display in order to render a corrected image which appears more in focus for a user with a visual impairment.

The processor may be adapted to determine the values of the subpixels of the pixelated display based on a location of a virtual image plane.

The location of the virtual image plane is related to the focal length of the eye of the user. If the user had perfect vision the virtual image plane would lie on the retina of the user or, alternatively, on the pixelated display. However, if the user does not have perfect vision the virtual image plane lies either in front of or behind of the retina of the user or, alternatively, in front of or behind of the pixelated display. Whether the location of the virtual image plane is assumed to be near the retina of the user or near the pixelated display depends on the methodology used by the processor to determine the values of the pixels. Either relative position may be used by the invention.

The processor is configured for determining a first location of the virtual image plane, which corresponds to a first viewing location of the eye of the user. The relative position of the virtual image plane may change if the relative position of the eye of the user changes with respect to the pixelated display. For example, the virtual image plane may move parallel to the pixelated display when the eye of the user moves parallel relative to the pixelate display. If the values of the subpixels of the display do not change accordingly the corrected image may appear less in focus to the user.

The first location of the virtual image plane is determined by the processor by comparing the focal length of the eye of the user to the first viewing location of the eye of the user. The focal length of the eye of the user is related to the visual impairment of the user. The focal length may be measured by conventional means and stored in the processor for use in the invention. The processor may also be configured for determining the focal length. For example the processor may determine from the focal length and the first viewing location whether a lens of the eye of the user projects a sharp image in a plane in front of or behind of the retina of the user. The location of this plane is the location of the virtual image plane. Alternatively the processor may determine from the focal length and the first viewing location whether a user may focus on a plane in front of or behind of the pixelated display. In this case the location of this plane is the location of the virtual image plane.

A virtual image is located on the virtual image plane. The virtual image corresponds to an image to be displayed on the pixelated display. For example, the virtual image may be a mirrored version of an image to be displayed on the display. The virtual image comprises virtual pixels which each have a corresponding virtual pixel value. The virtual pixel value determines the color of each virtual pixel. The virtual pixels are located on the virtual image plane.

The processor is configured for relating a subpixel of the pixelated display to a corresponding first virtual pixel of the virtual image plane. The processor may be determined to use a method, such as ray tracing, to determine a light path of a light ray emitted by the corresponding subpixel. The light path is determined between the corresponding subpixel, the microlens array, the retina of the eye of the user and the virtual image plane. The location on the virtual image plane where the light ray crosses the virtual image plane is the location of the first virtual pixel.

The processor is configured for determining a first value of the subpixel by comparing the value of the subpixel to the value of the first virtual pixel. The value of the first virtual pixel is determined by the virtual image. The processor is configured to operate the corresponding subpixel based on the respective first value determined for the subpixel when the eye of the user is in the first viewing location. By repeating these steps for each subpixel of the pixelated display an image may be displayed on the pixelated display that appears in focus for the user when the eye of the user is in the first viewing location.

The processor is preferably configured for determining a change in viewing location of the eye of the user based on a change in viewing location detected by the eye-tracking system. When the user moves away from the first viewing location the image displayed on the pixelated display may no longer appear to be in focus to the user. Thus the image has to be corrected and the values of the subpixels of the pixelated display have to be corrected for the image to appear in focus in a second viewing location.

The second viewing location is determined by the processor based on a change in viewing location detected by the eye-tracking system. The second viewing location is different from the first viewing location. The processor is further configured for determining a corresponding second location of the virtual image plane based on the second viewing location or, equivalently, based on the change of the viewing location from the first viewing location. The virtual image plane is between the first location and the second location when the eye of the user is between the first viewing location and the second viewing location. The virtual image is located on the virtual image plane irrespective of if the virtual image plane is in the first location or the second location.

When the eye of the user is in the second viewing location the processor is configured to relate the corresponding subpixel to a second virtual pixel of the virtual image plane. The processor is further configured for determining a second value of the corresponding subpixel of the pixelated display by comparing the value of the corresponding subpixel to a value of the second virtual pixel.

The processor is configured to operate the corresponding subpixel of the display based on the respective second value when the eye of the user is in the second viewing location.

In an embodiment wherein these steps are repeated for each subpixel of the pixelated display an image may be displayed on the pixelated display that appears in focus for the user when the eye of the user is in the second viewing location. The display device thus has compensated the image displayed on the pixelated display for the new location of the eye of the user. The invention thus allows an image to be compensated when the user moves to a second viewing location.

By repeating the steps when the eye of the user moves to a third viewing location the image will continue to appear in focus as viewed from the third viewing location. The invention thus allows the image displayed on the pixelated display to appear in focus irrespective of the viewing location and irrespective of movement of the eye of the user relative to the pixelated display. Thus the viewing experience is not negatively affected by movement relative to the pixelated display.

In embodiments it is possible that more than one light path of a light ray emitted by the corresponding subpixel exists between the corresponding subpixel, the microlens array, the retina of the eye of the user and the virtual image plane. In these embodiments one subpixel may correspond to multiple virtual subpixels. In these embodiments the value of the subpixel may be determined based on the first light path considered by the processor. In other embodiments the value of the subpixel may be determined based on the values of multiple virtual subpixels, e.g. based on an average value of the multiple subpixels.

A downside of determining which virtual pixel corresponds to a subpixel of the pixelated display for a given viewing location by determining a light path, e.g. by ray tracing, between the pixelated display and the virtual image plane is that this computation may be computationally intensive. As a result of this the corrected image displayed on the pixelated display may correct itself slower than desired. This may negatively impact the experience of the user. This problem may be larger if the pixelated display comprises more pixels and subpixels.

A known solution to this problem is to increase the computational power of the pixelated display and/or the corresponding smart device. However, this is limited by the hardware and other functionalities of the pixelated display and/or the smart device.

This problem is also present when a user moves to a second viewing location. In this case a second virtual pixel is to be determined that corresponds to the corresponding subpixel as the user is in the second viewing location. Determining the second virtual pixel for each subpixel of the display may be computationally intensive and require a lot of processor power. This may lead to a slower device and possible to an image that is corrected slower than desired.

This problem is alleviated by the display device according to claim 2. In this embodiment the processor is configured for relating the corresponding subpixel to the second virtual pixel of the virtual image plane by:
- determining, when the virtual image plane is in the first location, a first pixel location relative to the pixelated display of the corresponding first virtual pixel;
- comparing, when the virtual image plane is in the second location and for one or more of the virtual pixels, a location of the virtual pixels to the first pixel location; and
- relating the corresponding subpixel of the pixelated display to the virtual pixel whose location corresponds to the first pixel location when the virtual image plane is in the second location.

In this embodiment the second virtual pixel is determined by first determining a first pixel location of the first virtual pixel, second by comparing this first pixel location to locations of virtual pixels of the virtual image plane in the second location and third by relating the subpixel of the pixelate display to the virtual pixel whose location corresponds to the first pixel location.

For example, if the virtual image plane is shifted in a plane parallel to the pixelated display, such that the distance between the plane and the retina plane perpendicular to the pixelated display does not change, the virtual pixel whose second location corresponds to the first location of the first virtual pixel may be the virtual pixel whose second location is the first location.

For example, if the virtual image plane is moved in a direction perpendicular to the pixelated display, the virtual pixel whose second location corresponds to the first location of the first virtual pixel may be the pixel whose second location lies in the light path of the first virtual pixel.

Advantageously, in this embodiment it is not necessary to recalculate light paths of light rays emitted by the subpixels of the pixelate display. This reduces computational intensity significantly. As a result the display device may determine a corrected image faster so that the user experience is not affected negatively.

In an embodiment the processor is configured for determining:
- a parallel component of the first pixel location parallel to the pixelated display;
- a perpendicular component of the first pixel location perpendicular to the pixelated display;
- parallel components of the locations of each of the virtual pixels when the virtual image plane is in the second location; and
- perpendicular components of the locations of each of the virtual pixels when the virtual image plane is in the second location, and wherein the processor is configured for, when the perpendicular components are equal, relating the corresponding subpixel of the pixelated display to the virtual pixel whose parallel component is equal to the parallel component of the first pixel location.

Any location may be decomposed relative to the pixelated display in a coordinate component that is perpendicular to the pixelated display and a coordinate component that is parallel to the pixelated display. For example in a so called Cartesian coordinate decomposition. The system may also use other types of coordinate system such as polar coordinate systems.

When the perpendicular component of the first pixel location and the perpendicular components of the location of one of the virtual pixels are equal, when the virtual image plane is in the second location, the first virtual pixel and the respective virtual pixel are corresponding virtual pixels if the parallel components are the same.

In an embodiment the processor is configured for relating the corresponding subpixel of the pixelated display to the virtual pixel whose parallel component is equal to the parallel component of the first pixel location when the eye-tracking system does not detect a change of the eye of the user in a perpendicular direction relative to the pixelated display.

The processor may determine that the perpendicular component of the first virtual pixel location and the perpendicular components of the locations of each of the virtual pixels, in the second location, are equal when the eye-tracking system does not detect a change in position in a direction perpendicular to the pixelated display. Thus in this embodiment the processor may not have to compare the perpendicular components directly, saving computational time.

In an embodiment the display device is adapted to provide a feedback, e.g. a haptic feedback, to the user, e.g. prompting the user to change the position of the pixelated display. For example, the system may provide a feedback when the user moves too far away or too close to the pixelated display for example such that the display device cannot properly render an image that appears in focus for the user. In another example, a feedback may be provided to a user prompting the user to keep the display device stable.

In an embodiment the eye-tracking system is further adapted for tracking a gaze of the eye of the user for determining at which part of the pixelated display the user is gazing. In display devices, in particular in display devices with larger displays, the user is often not focused on the entire display but rather at a part of the display. It may therefore be advantageous to not correct an image on the entire display but rather only part of the image where the user is gazing. Additionally tracking a gaze of the user may provide information on if the user is gazing at the display at all. In some examples the user may not be gazing at the display, and no image correction needs to take place.

In a further embodiment the corresponding subpixel is located in the part of the pixelated display at which the user is gazing. In this embodiment the image is corrected in the part of the pixelated display where the user is gazing. In particular, in an embodiment the processor is configured for relating each subpixel in the part of the pixelated display where the user is gazing to a corresponding first virtual pixel and to a corresponding second virtual pixel.

In an embodiment the display device is adapted for tracking a pupil size of a pupil of the eye of the user. For example, when the pupil size increases more information displayed on the pixelated display may fall into the eye of the user. Thus a larger portion of the image may need to be corrected. The pupil size of the user may be influenced by adjusting brightness of the display, e.g. at night.

In an embodiment of the display device the microlens width and/or the microlens height is equal or smaller than a pitch of 8 subpixels of the pixelated display. A smaller lens size may lead to a sharper image with less distortion effects due to the lenses. Advantageously the lens size is such that a moiré effect is avoided, for example wherein the moiré effect may be avoided when the lens size is not three times the pitch of the subpixels.

In an embodiment the display device is further provided with an optical gap layer, which is provided between the pixelated display and the microlens array, wherein the optical gap layer defines an optical gap between the pixelated display and the microlens array. The optical gap layer allows to increase or decrease the incidence angle of a light ray emitted by a subpixel of the display with the microlenses. A decrease of the incidence angle may be achieved by increasing the size of the optical gap. Similarly, an increase of the incidence angle may be achieved by decreasing the size of the optical gap.

In an embodiment the eye-tracking system is adapted for determining a viewing distance of the user relative to the pixelated display. This may be combined with a feedback system, when the viewing distance becomes too great or too small a feedback may be sent to the user to urge the user to change the viewing distance. Keeping the display device at a preferred viewing distance may increase the focus of the image as observed by the user. Additionally keeping the display device at a preferred distance may increase the amount of information observed by the user because, e.g. a larger portion of the display may be observed by the user.

In an embodiment wherein an optical gap layer is present a refractive index of the microlenses of the microlens array is higher than a refractive index of the optical gap layer.

In an embodiment, wherein an optical gap layer is present, for each lens of the microlens array, the relation:

$$\text{smaller(microlens width,microlens height)/optical gap}-\text{pupil diameter}-\text{point projection diameter})/\text{object distance}$$

is minimized, wherein the smaller of the corresponding microlens width and microlens height is denoted by smaller (microlens width, microlens height), an estimate for the pupil size of the user is denote by pupil diameter, a size of a projection of an arbitrary point within a subpixel on the plane in which the pupil of the eye lies is denoted by point projection diameter, and a distance from the pixelated display to the eye of the user is denoted by object distance.

The above relation, when the value is smaller but greater or equal to zero, allows for a larger number of subpixels to be projected onto the retina of the user compared to when the relation gives a larger number. A result is that the user views the pixelated display, not only in focus, but also with a higher resolution.

The microlens width, microlens height, and optical gap may all be determined during construction of the display device. The pupil diameter of the user may be approximated based on ambient light conditions or it may be determined based on measurements of the eye of the user. The point projection diameter and the object distance depend on the distance of the eye of the user to the display device. Thus the relation may be minimized by changing the distance to the display. This determines an optimal viewing distance. The display device may provide feedback, e.g. haptic feedback, to the user in order to encourage the user to keep the display at the optimal viewing distance.

In an embodiment wherein an optical gap layer is present the focal length of the lenses in the microlens array is equal to the optical gap.

In an embodiment wherein an optical gap layer is present the optical gap comprises a secondary microlens array.

In an embodiment the microlenses are rectangular microlenses.

In an embodiment the microlenses are square microlenses. In an embodiment the microlenses are circular or ellipsoidal microlenses. In an embodiment the microlenses are hexagonal microlenses.

In an embodiment the display device further comprises a protection layer which is placed on top of the microlens array. The protection layer may comprise a plastic see through layer which is placed on top of the microlens array to protect the microlenses and the pixelated display e.g. against scratches and dirt.

In an embodiment the pixelated display is provided in a smart phone case. For example, the entire display device is integrated in a smart phone case. In this embodiment the pixelated display may be integrated in the smart phone case such that the pixelated display is located adjacent to or on top of a display of the smart phone. For example, the pixelated display may mirror the information on the display of the smart phone.

The invention is further related to a method for displaying an image for a user having a visual impairment wherein use is made of a display device according to the invention, the display device comprising:

a pixelated display comprising an array of pixels, each pixel comprising a number of subpixels, and wherein the pixelated display is operable to display the image to an eye of the user located at a viewing location relative to a position of the pixelated display;

a processor for operating the pixels of the pixelated display to display the image on the pixelated display wherein the processor is operable to store information on the eye of the user focal length of the eye;

an eye-tracking system adapted for determining changes in the viewing location of the eye of the user relative to the position of the pixelated display, wherein, preferably, the processor is configured for determining the change in viewing location of the eye of the user based on the change in viewing location detected by the eye-tracking system; and a microlens array provided on the pixelated display, wherein the microlens array comprises microlenses that are arranged in a two-dimensional plane oriented parallel to the pixelated display, wherein the microlens array covers, preferably completely covers, the pixelated display, and wherein the microlens array is configured to project light emitted by the pixelated display towards the eye of the user in the viewing location, wherein the processor is configured for determining a first location of a virtual image plane, corresponding to a first viewing location of the eye of the user, by comparing the focal length of the eye of the user to the first viewing location, wherein a virtual image is located on the virtual image plane which virtual image corresponds to an image to be displayed on the pixelated display, wherein the virtual image determines values of virtual pixels of the virtual image plane, wherein the processor is configured for relating a subpixel of the pixelated display to a corresponding first virtual pixel of the virtual image plane by determining between the corresponding subpixel, the microlens array, the retina of the eye of the user, and the first virtual pixel a light path of a light ray emitted by the corresponding subpixel, wherein the processor is further configured for determining a first value of the corresponding subpixel of the pixelated display by comparing the value of the corresponding subpixel to the value of the first virtual pixel, wherein the processor is configured to operate the corresponding subpixel of the display based on the respective first value when the eye of the user is in the first viewing location, wherein the processor is configured for determining a second location of the virtual image plane, corresponding to a second viewing location of the eye of the user, when the eye tracking system determines a change in the viewing location of the eye of the user from the first viewing location to the second viewing location, wherein the processor is further configured to relate the corresponding subpixel of the pixelated display to a second virtual pixel of the virtual image plane when the virtual image plane is in the second location, wherein the processor is further configured for determining a second value of the corresponding subpixel of the pixelated display by comparing the value of the corresponding subpixel to a value of the second virtual pixel; and wherein the processor is configured to operate the corresponding subpixel of the display based on the second value when the eye of the user is in the second viewing location.

Using alternative wording for the method described above the invention is further related to a method for displaying an image for a user having a visual impairment wherein the image is displayed on a display device according to the invention.

In an embodiment the method comprises:
determining a first location of a virtual image plane by comparing the focal length of the eye of the user to the viewing location, wherein a virtual image is located on the virtual image plane which virtual image corresponds to an image to be display on the pixelated display, wherein the virtual image determines values of virtual pixels of the virtual image plane;
relating a subpixel of the pixelated display to a corresponding first virtual pixel of the virtual image plane by determining between the corresponding subpixel, the microlens array, the retina of the eye of the user, and the first virtual pixel a light path of a light ray emitted by the corresponding subpixel;
determining a first value of the corresponding subpixel of the pixelated display by comparing the value of the corresponding subpixel to the value of the first virtual pixel;
operating the corresponding subpixel of the display based on the respective first value when the eye of the user is in the first viewing location;
determining a second location of the virtual image plane, corresponding to a second viewing location of the eye of the user, based on a change in the viewing location of the eye of the user determined by the eye-tracking system;
relating the corresponding subpixel of the pixelated display to a second virtual pixel of the virtual image plane when the virtual image plane is in the second location;
determining a second value of the corresponding subpixel of the pixelated by comparing the value of the corresponding subpixel to a value of the second virtual pixel; and
operating the corresponding subpixel of the display based on the second value when the eye of the user is in the second viewing location.

In an embodiment the method further comprises:
determining a first pixel location relative to the pixelated display of the corresponding first virtual pixel with the virtual image plane in the first location;
comparing, when the virtual image plane is in the second location and for one or more of the virtual pixels, a location of each of the virtual pixels to the first pixel location; and
relating the corresponding subpixel of the pixelated display to the virtual pixel whose location corresponds to the first pixel location when the virtual image plane is in the second location.

In an embodiment the method comprises:
providing a feedback, e.g. a haptic feedback, to the user, e.g. prompting the user to change the position of the pixelated display.

In an embodiment the method comprises:
tracking the location of the eye of the user by the eye-tracking system in a direction perpendicular to the pixelated display;
changing the first location of the virtual image plane based on a change in a location of the eye of the user in the direction perpendicular to the pixelated display.

In an embodiment the method comprises:
tracking a gaze of the eye of the user by the eye-tracking system for determining at which part of the pixelated display the user is looking;
wherein the corresponding subpixel is located in the part of the pixelated display at which the user is gazing.

The invention is further related to a processor for operating a display device adapted for displaying an image for a user having a visual impairment according to the invention.

The invention is further related to a computer program for performing the method according to the invention.

The invention is further related to a smart phone case comprising a pixelated display according to the invention and adapted for operating the pixelated display according to the method of the invention.

The invention will now be described in a non-limiting way by reference to the accompanying drawings in which like parts are indicated by like reference symbols and in which.

Figure 1:
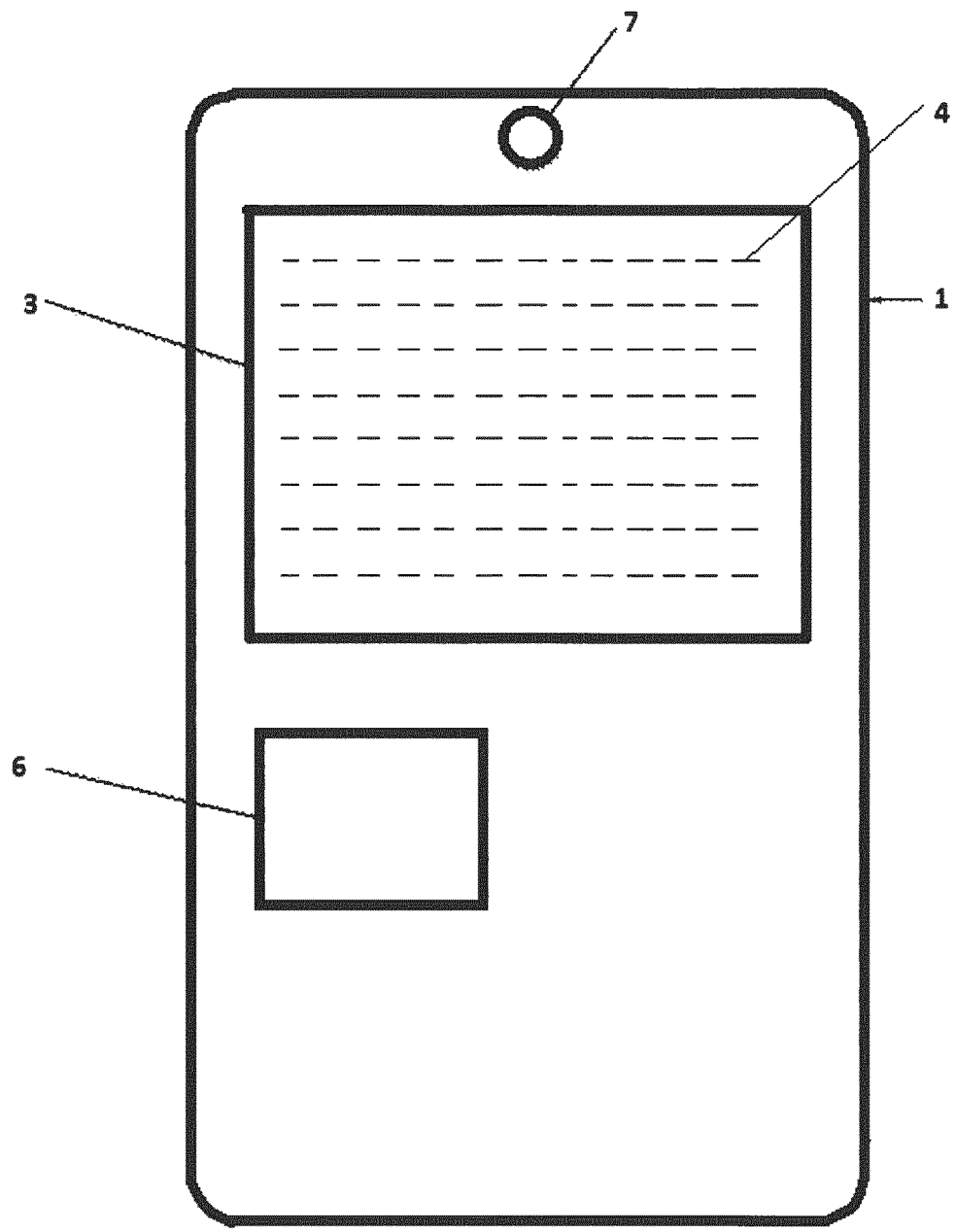
FIG. 1 depicts a display device comprising a pixelated display.

FIG. 1 depicts a display device 1 comprising a pixelate display 3. The pixelated display 3 comprises a number of pixels 4 which are schematically shown in FIG. 1. By emitting light at certain frequencies the pixels 4 may render an image 2 on the pixelated display 4. Each pixel 4 of the pixelated display 3 comprises a number, for example three, subpixels 13 which are not shown in FIG. 1.

The display device 1 further comprises a processor 6 for operating the pixels 4, e.g. by operating the subpixels 13. By operating the pixels 4 the image 2 may be displayed on the pixelated display 3. The processor is further operable to store information on the eye 5 of the user such as the focal length of the eye 5 of the user, the size of the eye 5 of the user, or the size of the pupil of the eye 5. This information may then be used by the processor 6 to determine values for the pixels 4, e.g. for the subpixels 13, to render the image 2 in a way that appears sharp to the user having the visual impairment.

The display device 1 further comprises an eye tracking system 7 adapted for determining changes in the viewing location of the eye 5 of the user relative to the position of the pixelated display 3. In other words the eye tracking system 7 tracks movement of the eye 5 of the user relative to the pixelated display 3.

The display device 1 of FIG. 1 is depicted wherein the pixelated display 3, the processor 6 and the eye-tracking system 7 all form part of the same apparatus. This is not necessarily the case, for example the processor 6 may be in a different location and communicate with the eye-tracking system 7 and the pixelated display 3 remotely, e.g. via internet or Bluetooth.

Figure 2:
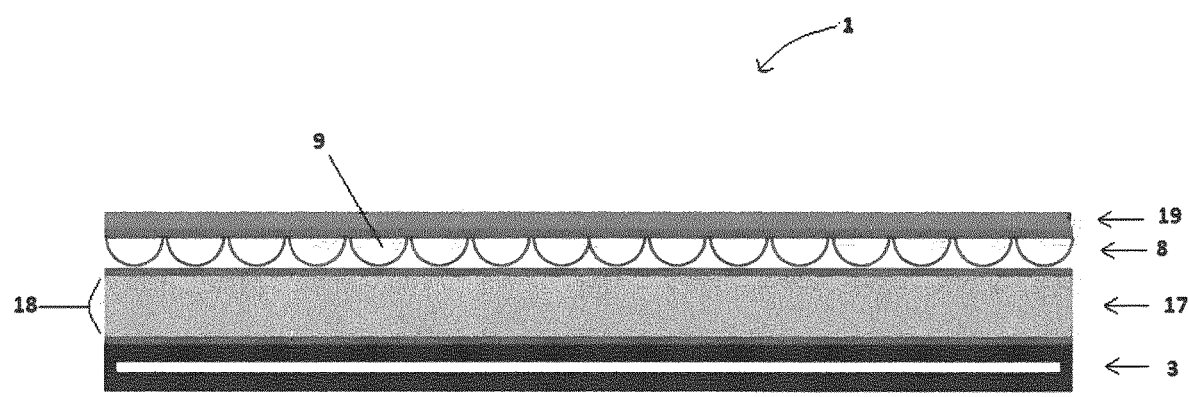
FIG. 2 depicts a side view of a pixelated display covered by a microlens array.

FIG. 2 depicts a side view of a pixelated display 3 covered by a microlens array 8. The microlens array 8 is separated from the pixelated display 3 by an optical gap layer 17 which defines an optical gap 18 between the pixelated display 3 and the microlens array.

Figure 3:
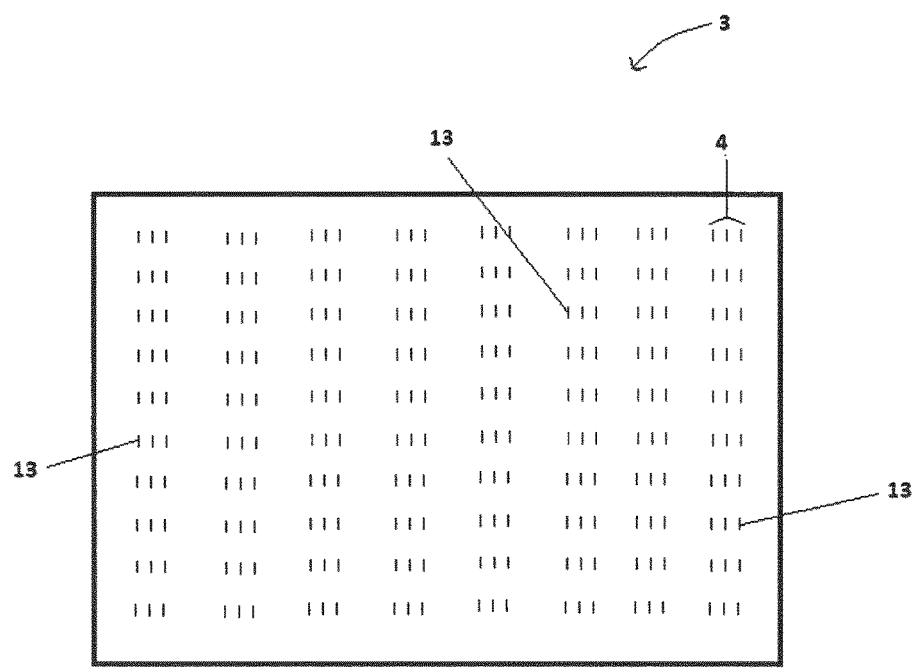
FIG. 3 depicts a front view of a pixelated display schematically showing a number of pixels and subpixels.

The microlens array 8 comprises a number of microlenses 9. The microlenses 9 of FIG. 3 are depicted as plano-convex. However other types of microlenses 9 may be used. The microlenses 9 may vary in shape, microlens width and microlens height. In embodiments the focal length of the microlenses 9 is substantially equal to the optical gap layer 17 such that the pixelated display 3 lies at the focal length of the microlens array 8. In embodiments the microlens array 8 may be covered by a protection layer 19 such as a translucent plastic layer to protect the microlenses 9 from e.g. scratches and dust.

FIG. 3 depicts a front view of a pixelated display 3 schematically showing a number of pixels 4 and subpixels 13. Each pixel 4 of the pixelated display 3 in FIG. 3 comprises three subpixels 13. For example each subpixel corresponds to another color channel such as red, green and blue. By emitting light with different values from these subpixels 13 the pixels 4 may appear to emit light at any wavelength. Thus this allows an image 2 to be displayed on the pixelated display 3.

Figure 4:
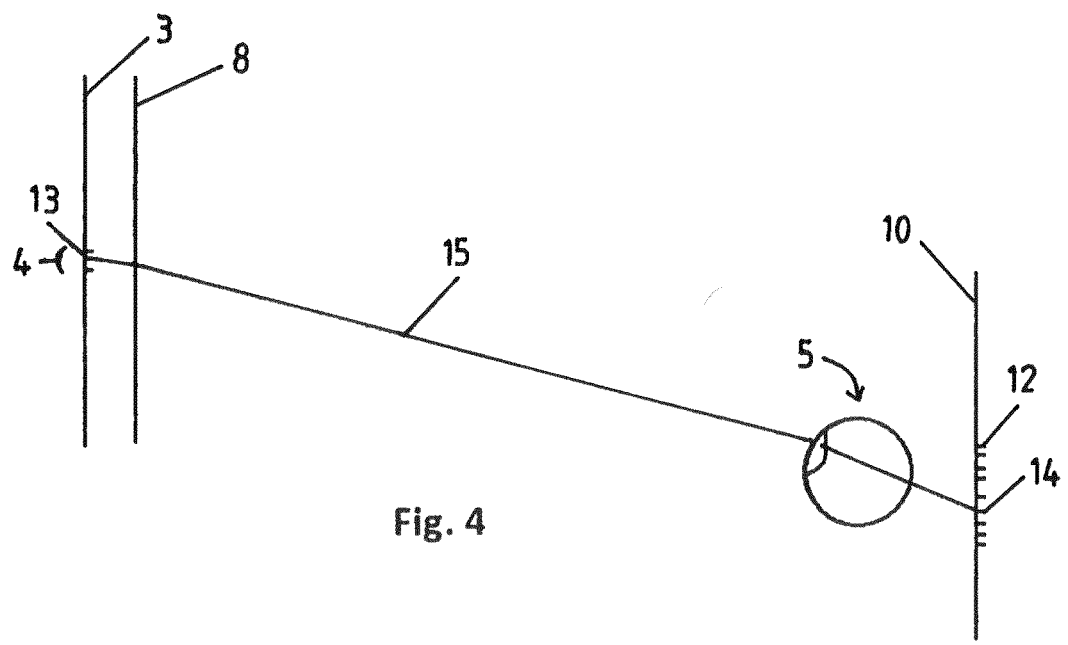
FIG. 4 depicts a schematic view of a light path between the pixelated display and the virtual image plane behind the eye of the user.

FIG. 4 depicts a schematic view of a light path 15 between the pixelated display 3 and the virtual image plane 10 behind the eye 5 of the user. The pixelated display 3 comprises a pixel 4 which comprises a number of subpixels 13. One of the subpixels 13 emits a light ray which travels along the light path 15 through the microlens array 8 and towards the eye 5 of the user. The processor 6 determines the light path 15 from the pixelated display 3 through the eye 5 of the user to the virtual image plane 10 using a technique such as ray tracing.

The virtual image plane 10 comprises a number of virtual pixels 12 whose values are determined by a virtual image 11 which is placed on the virtual image plane 10. The location of the virtual image plane 10 is determined by the processor 6 by comparing the focal length of the eye 5 of the user to the location wherein the eye 5 is, e.g. the first viewing location.

The light path 15 crosses the virtual image plane 10 in one of the virtual pixels 12. This may determine which of the virtual pixels 12 is the first virtual pixel 14. The value of the first virtual pixel 14 determines a value of the corresponding subpixel 13 when the eye of the user 5 is in the corresponding viewing location, e.g. in the first viewing location.

By determining a light path 15 for multiple subpixels 13 a value of each of these subpixels is determined by corresponding first virtual pixels 14. In this way a corrected image 2 may be displayed on the pixelated display 3 by the display device 1 which appears in focus to the user, e.g. based on the focal length of the eye 5 of the user, e.g. which focal length is effected by the visual impairment of the user.

Figure 5:
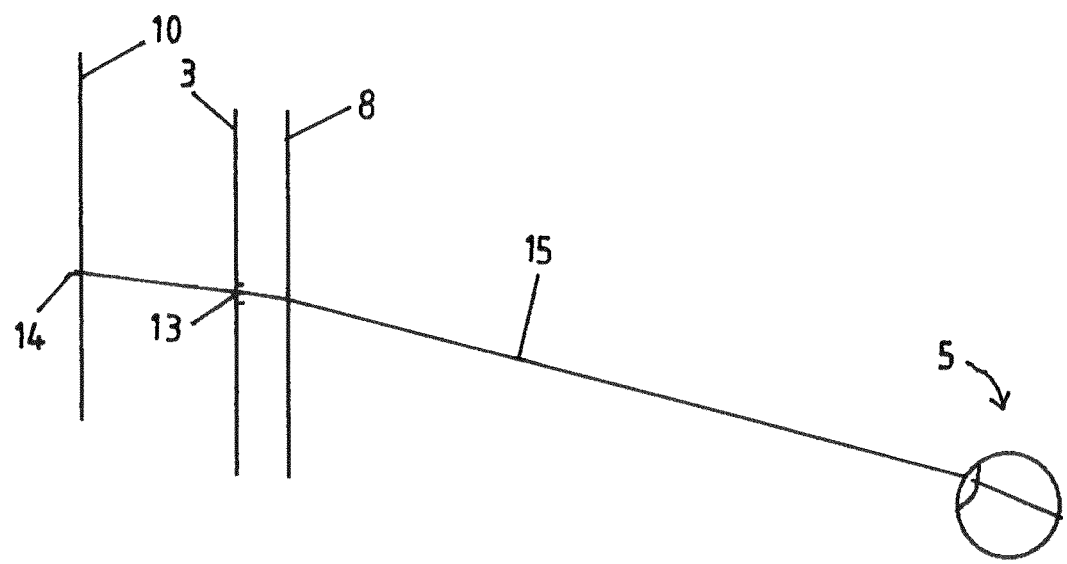
FIG. 5 depicts a schematic view of a light path between the pixelated display, the eye of the user and the virtual image plane behind the pixelated display.

FIG. 5 depicts a schematic view of a light path 15 between the pixelated display 3, the eye of the user and the virtual image plane 10 which is located behind the pixelated display 3. This embodiment shows an alternative method of finding a first virtual pixel 14 corresponding to a subpixel 13.

In FIG. 5 the virtual image plane 10 is located behind the pixelated display 3. In this case a light path 15 is determined by the processor 6 from the virtual image plane 10, through the pixelated display 3 and the microlens array 8, to the eye 5 of the user. This allows a corresponding virtual pixel 12, e.g. a corresponding first virtual pixel 14 if the eye 5 of the user is in the first viewing location, to be found for each subpixel 13 of the pixelated display 3.

Figure 6:
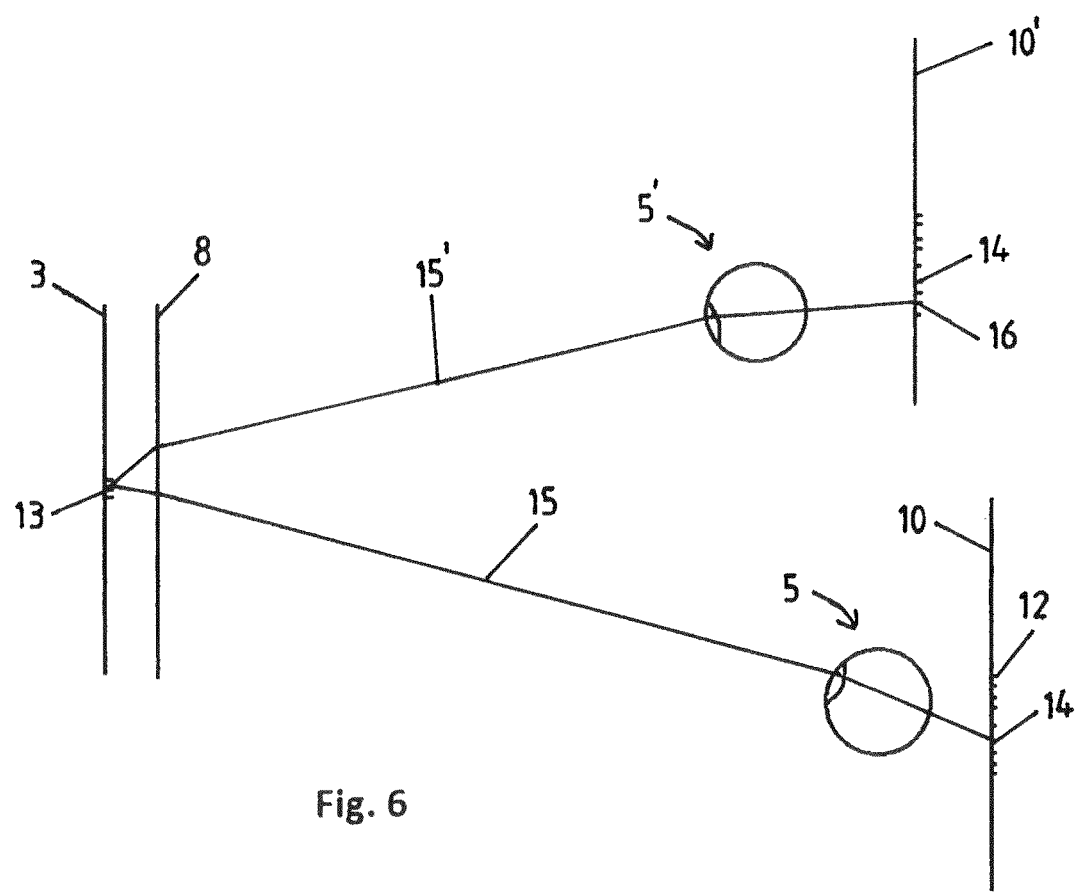
FIG. 6 depicts a schematic view of the eye of the user in a first viewing location and the eye of the user in a second viewing location.

FIG. 6 depicts a schematic view of the eye 5 of the user in a first viewing location and the eye 5' of the user in a second viewing location. The change in location of the eye 5, 5' has been detected by the eye-tracking system 7, and a second virtual pixel 16 is related to the corresponding subpixel 13 by the processor 6. In an embodiment of the invention the second virtual pixel 16 is related to the corresponding subpixel 13 by a light path 15'. The light path 15' is between the subpixel 13 and the virtual image plane 10' in the second location thereof.

The processor 6 is configured for determining a second value of the corresponding subpixel 13 of the pixelated display 3 by comparing the value of the corresponding subpixel 13 to a value of the second virtual pixel 16. The processor 6 is further configured to operate the corresponding subpixel 13 of the display 3 based on the second value when the eye 5' of the user is in the second viewing location.

In another embodiment the second virtual pixel 16 is not determined by relating the second virtual pixel 16 to the subpixel 13 by a light path 15'. In this embodiment a first pixel location of the first virtual pixel 12 is determined when the virtual image plane 10 is in the first location. A location of the virtual pixels 12 is compared to this first pixel location when the virtual image plane 10 is in the second location. The subpixel 13 of the display 3 is then related to the virtual pixel 16 whose location corresponds to the first pixel location when the virtual image plane 10' is in the second location.

Advantageously, in this embodiment it is not necessary to recalculate light paths 15' of light rays emitted by the subpixels 13 of the pixelate display. This reduces computational intensity significantly. As a result the display device 1 may determine a corrected image 2 faster so that the user experience is not affected negatively when the eye 5 of the user moves relative to the pixelated display 3.

Figure 7:
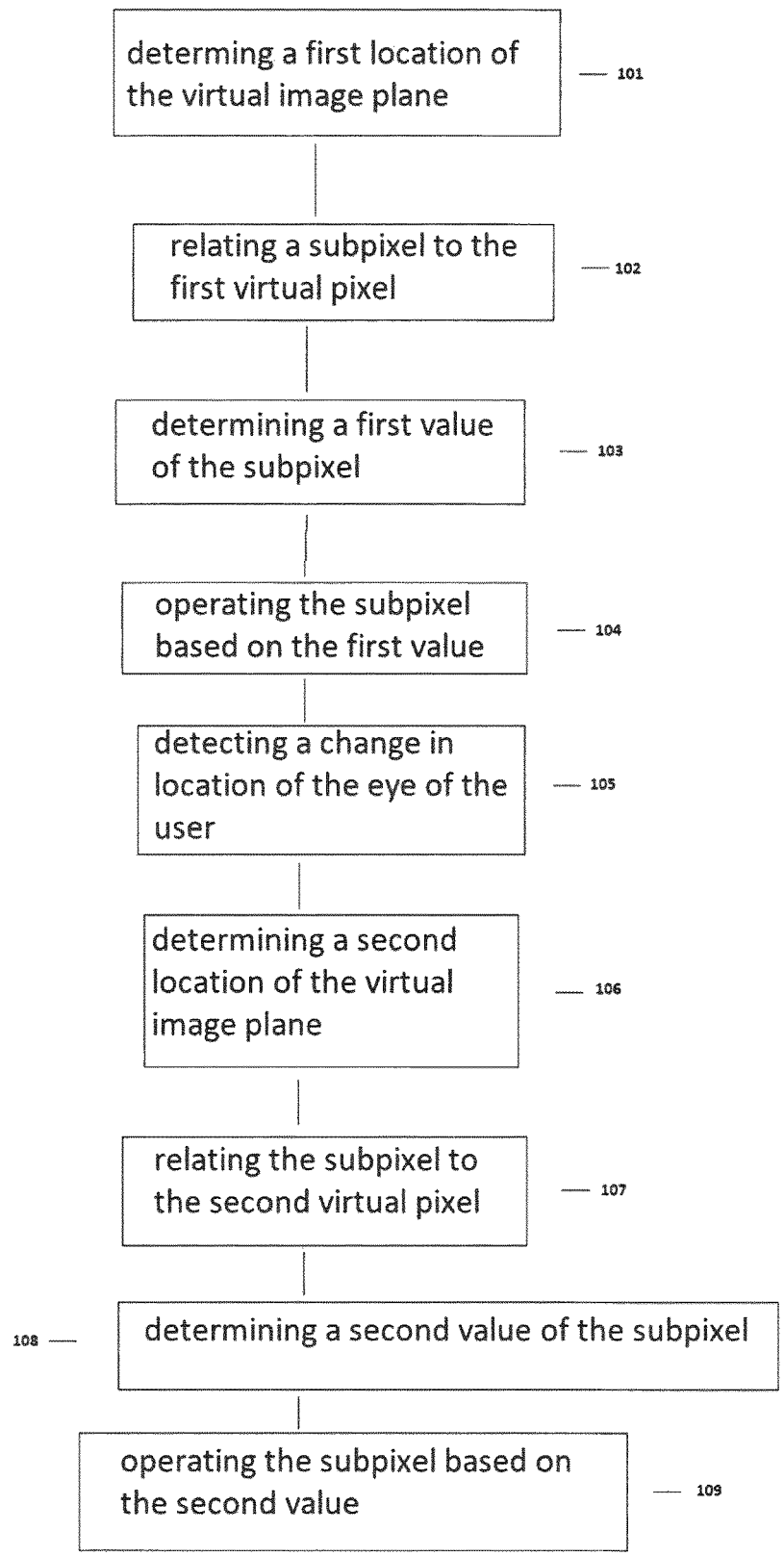
FIG. 7 depicts a flow chart of the method for displaying an image on the pixelated display.

FIG. 7 depicts a flow chart of the method for displaying an image 2 on the pixelated display 3. The first step 101 of the method is to determine a first location of the virtual image plane 10 by comparing the focal length of the eye 5 of the user to the viewing location. A virtual image 11 may be located on the virtual image plane 10. The virtual image 11 corresponds to an image 2 to be displayed on the pixelated display 3 and the virtual image 11 determines values of virtual pixels 12 of the virtual image plane 10.

The second step 102 of the method relates a subpixel 13 of the pixelated display 3 to a corresponding first virtual pixel 12 of the virtual image plane 10 by determining between the corresponding subpixel 13, the microlens array 8, the retina of the eye 5 of the user, and the first virtual pixel 14 a light path 15 of a light ray emitted by the corresponding subpixel.

The third step 103 of the method is determining a first value of the corresponding subpixel 13 of the pixelated display 3 by comparing the value of the corresponding subpixel 13 to the value of the first virtual pixel 14.

The fourth step 104 of the method is operating the corresponding subpixel 13 of the display 3 based on the respective first value when the eye 5 of the user is in the first viewing location.

The fifth step 105 of the method is detecting a change in location of the eye 5 of the user by the eye-tracking system 7.

The sixth step 106 of the method is determining a second location of the virtual image plane corresponding to a second viewing location of the eye 5 of the user, based on the change in the viewing location of the eye 5 of the user determined by the eye-tracking system 7. Wherein the second viewing location of the eye 5 of the user is different from the first viewing location.

The seventh step 107 of the method is relating the corresponding subpixel 13 of the pixelated display to a second virtual pixel 16 of the virtual image plane 10 when the virtual image plane is in the second location.

The eight step 108 of the method is determining a second value of the corresponding subpixel 13 of the pixelated display 3 by comparing the value of the corresponding subpixel 13 to a value of the second virtual pixel 16.

The ninth step 109 of the method is operating the corresponding subpixel 13 of the display 3 based on the second value when the eye 5 of the user is in the second viewing location.

This method the user to move relative to the display device 1 without the user having a negative impact on the viewing experience as a result of viewing the corrected image 2 from different angles. The user may experience a negative impact on the viewing experience because the ability of the user to view the image 2 in focus is reduced depending on the viewing angle.

In embodiments wherein method steps 107-109 are repeated for each subpixel 13 of the pixelated display 3 an image 2 may be displayed on the pixelated display 3 that appears in focus for the user when the eye 5 of the user is in the second viewing location. The display device 1 thus has compensated the image 2 displayed on the pixelated display 3 for the new location of the eye 5 of the user. The invention thus allows an image 2 to be compensated when the user moves to a second viewing location.

By repeating the method steps 105-109 when the eye 5 of the user moves to a third viewing location the image 2 will continue to appear in focus as viewed from the third viewing location. The invention thus allows the image 2 displayed on the pixelated display 3 to appear in focus irrespective of the viewing location and irrespective of movement of the eye 5 of the user relative to the pixelated display 3. Thus the viewing experience is not negatively affected by movement relative to the pixelated display 3.

Figure 8:
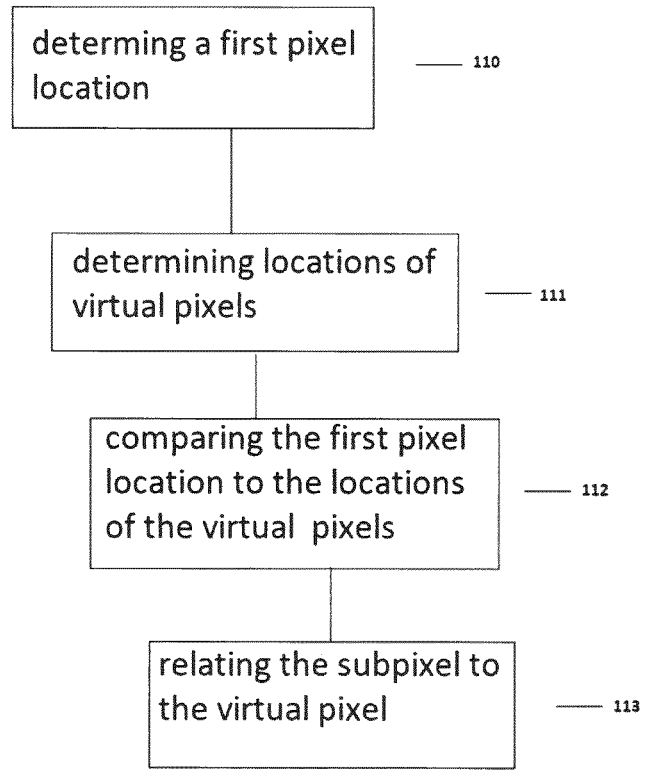
FIG. 8 depicts a flow chart of a method for determining a second virtual pixel.

FIG. 8 depicts a flow chart of a method for determining a second virtual pixel 16 which may be performed while performing method steps 101-107. The first step 110 is determining a first pixel location relative to the pixelated display 3 of the corresponding first virtual pixel 14 when the virtual image plane 10 is in the first location.

The second method step 111 is determining a location of one or more of the virtual pixels 12 when the virtual image plane 10' is in the second location.

The third method step 112 is comparing, when the virtual image plane 10' is in the second location and for one or more of the virtual pixels 12, a location of each of the virtual pixels 12 to the first pixel location.

The fourth method step 113 is relating the corresponding subpixel 13 of the pixelated display 3 to the virtual pixel 16 whose location corresponds to the first pixel location when the virtual image plane 10' is in the second location.

The invention claimed is:

1. A display device for displaying an image to a user having a visual impairment, the display device comprising:
   a pixelated display comprising a plurality of pixels, each pixel comprising a plurality of subpixels;
   an eye-tracking system for tracking a position of an eye of a user relative to the pixelated display;
   a microlens array provided on the pixelated display; and
   a processor;
   wherein the processor is configured to:
   determine, based on a focal length of the eye, a location of a virtual image plane, the virtual image plane corresponding to a viewing location of the eye and comprising a plurality of virtual pixels;
   relate, for each subpixel, the subpixel to a corresponding virtual pixel of the virtual image plane by determining a path of a light ray emitted by the subpixel to the corresponding virtual pixel,
   determine, for each subpixel, a first value of the subpixel by comparing a value of the subpixel to a value of its corresponding virtual pixel,
   operate each subpixel based on the determined first value to display a corrected image on the pixelated display.

2. The display device according to claim 1, wherein the processor is further configured to:
   determine, based on a detected change a change in a location of the eye to a second viewing location, a second location of the virtual image plane;
   relate, for each subpixel, the subpixel to a second virtual pixel of the virtual image plane when the virtual image plane is in the second location;
   determine, for each subpixel, a second value of the subpixel by comparing the value of the corresponding subpixel to a value of the second virtual subpixel; and
   operate each subpixel based on the determined second value to display an updated corrected image on the pixelated display.

3. The display device according to claim 1, wherein the display device is configured to provide a feedback to the user to prompt the user to change a position of the pixelated display.

4. The display device according to claim 1, wherein the eye-tracking system is configured to track a gaze of the eye of the user to determine at which part of the pixelated display the user is gazing.

5. The display device according to claim 4, wherein the corresponding subpixel is located in the part of the pixelated display at which the user is gazing.

6. The display device according to claim 1, wherein the display device is further provided with an optical gap layer between the pixelated display and the microlens array, wherein the optical gap layer defines an optical gap between the pixelated display and the microlens array.

7. The display device according to claim 6, wherein the focal length of the microlenses in the microlens array is equal to the size of the optical gap.

8. The display device according to claim 6, wherein the optical gap comprises a secondary microlens array.

9. The display device according to claim 1, wherein the microlenses are rectangular or square microlenses.

10. The display device according to claim 1, wherein the display device further comprises a protection layer on top of the microlens array.

11. The display device according to claim 1, wherein the pixelated display is provided in a smart phone case.

12. A method for displaying an image to a user having a visual impairment, the method comprising:
   determining, based on a focal length of an eye of the user, a location of a virtual image plane, the virtual image plane corresponding to a viewing location of the eye and comprising a plurality of virtual pixels;
   relating, for each subpixel of a pixelated display, the subpixel to a corresponding virtual pixel of the virtual image plane by determining a path of a light ray emitted by the subpixel to the corresponding virtual pixel,
   determining, for each subpixel, a first value of the subpixel by comparing a value of the subpixel to a value of its corresponding virtual pixel,
   operating each subpixel based on the determined first value to display a corrected image on the pixelated display.

13. The method according to claim 12, wherein the method further comprises:
   determining, based on a detected change a change in a location of the eye to a second viewing location, a second location of the virtual image plane;
   relating, for each subpixel, the subpixel to a second virtual pixel of the virtual image plane when the virtual image plane is in the second location;
   determining, for each subpixel, a second value of the subpixel by comparing the value of the corresponding subpixel to a value of the second virtual subpixel; and
   operating each subpixel based on the determined second value to display an updated corrected image on the pixelated display.

14. The method according to claim 12, further comprising providing a feedback to the user to prompt the user to change a position of the pixelated display.

15. The method according to claim 12, further comprising tracking a gaze of the eye of the user to determine at which part of the pixelated display the user is gazing.

16. A smart phone case comprising the display device according to claim 1 and adapted for operating the display device according to the method according to claim 12.

* * * * *